United States Patent
Brown et al.

(10) Patent No.: US 6,723,092 B2
(45) Date of Patent: Apr. 20, 2004

(54) ATRIAL FIBRILLATION RF TREATMENT DEVICE AND METHOD

(75) Inventors: Tony R. Brown, 6605 E. Canyon Hills Rd., Anaheim Hills, CA (US) 92807; Hein Nguyen, Santa Ana, CA (US); Suresh Wadhwani, Mission Viejo, CA (US); Octavio V. Adame, Guadalajara (MX); Michael D. Laufer, Menlo Park, CA (US)

(73) Assignee: Tony R. Brown, Anaheim Hills, CA (US)

( * ) Notice: Subject to any disclaimer, the term of this patent is extended or adjusted under 35 U.S.C. 154(b) by 56 days.

(21) Appl. No.: 10/024,672

(22) Filed: Dec. 17, 2001

(65) Prior Publication Data

US 2002/0120263 A1 Aug. 29, 2002

Related U.S. Application Data

(60) Provisional application No. 60/287,798, filed on Apr. 30, 2001, and provisional application No. 60/256,245, filed on Dec. 15, 2000.

(51) Int. Cl.⁷ .............................................. A61B 18/18
(52) U.S. Cl. ............................ 606/41; 606/51; 607/102
(58) Field of Search ............................. 606/41, 42, 45, 606/46, 48–52; 607/101, 102

(56) References Cited

U.S. PATENT DOCUMENTS

| | | | |
|---|---|---|---|
| 4,016,886 A | | 4/1977 | Doss et al. |
| 5,281,218 A | | 1/1994 | Imran |
| 5,403,311 A | * | 4/1995 | Abele et al. .................. 606/49 |
| 5,443,463 A | | 8/1995 | Stern et al. |
| 5,472,441 A | * | 12/1995 | Edwards et al. .............. 606/41 |
| 5,823,197 A | | 10/1998 | Edwards |
| 5,827,268 A | | 10/1998 | Laufer |
| 5,879,349 A | | 3/1999 | Edwards |
| 5,895,417 A | | 4/1999 | Pomeranz et al. |
| 5,919,200 A | | 7/1999 | Stambaugh et al. |
| 5,928,224 A | | 7/1999 | Laufer |
| 5,938,659 A | * | 8/1999 | Tu et al. ........................ 606/41 |
| 5,941,845 A | | 8/1999 | Tu et al. |
| 5,944,715 A | | 8/1999 | Goble et al. |
| 5,989,284 A | | 11/1999 | Laufer |
| 6,004,316 A | | 12/1999 | Laufer |
| 6,030,384 A | * | 2/2000 | Nezhat ......................... 606/48 |
| 6,071,303 A | | 6/2000 | Laufer |
| 6,077,257 A | | 6/2000 | Edwards et al. |
| 6,083,219 A | | 7/2000 | Laufer |
| 6,086,586 A | | 7/2000 | Hooven |

(List continued on next page.)

FOREIGN PATENT DOCUMENTS

WO     WO 01/80724     4/2001

*Primary Examiner*—Michael Peffley

(57) ABSTRACT

An RF treatment device according to the present invention includes one or two radio frequency electrode holders each having multiple electrodes arranged to create a transmural lesion through tissue. The treatment device is placed with one holder placed on the endocardial surface of the heart wall with the electrodes protruding towards the epicardial surface of the heart and the other optional holder placed on the epicardial surface of the heart with the electrodes protruding towards the endocardial surface of the heart forming a bipolar arrangement of equally spaced electrodes. The embodiments of the present invention are described for use in creating a transmural lesion in heart tissue to treat atrial fibrillation by blocking the passage of abnormal electrical currents through the heart. However, the devices and methods may also be used to create continuous transmural lesions in heart tissue and other body organs and tissues to treat other conditions. Although the invention is primarily described with respect to the application of RF bi-polar energy, the devices may also be used to apply other types of energy, such as cryo, ultrasound, microwave, heat, or other electrical means of providing an interruption to the abnormal electrical circuits at given regions.

39 Claims, 12 Drawing Sheets

U.S. PATENT DOCUMENTS

| | | |
|---|---|---|
| 6,106,520 A | 8/2000 | Laufer et al. |
| 6,113,596 A | 9/2000 | Hooven et al. |
| 6,129,724 A | 10/2000 | Fleischman et al. |
| 6,152,139 A | 11/2000 | Laufer |
| 6,152,923 A | 11/2000 | Ryan |
| 6,162,220 A | 12/2000 | Nezhat |
| 6,212,433 B1 | 4/2001 | Behl |
| 6,283,935 B1 | 9/2001 | Laufer et al. |
| 6,497,704 B2 * | 12/2002 | Ein-Gal .................. 606/41 |
| 6,517,536 B2 * | 2/2003 | Hooven et al. ........... 606/41 |
| 2001/0031961 A1 | 10/2001 | Hooven |
| 2002/0120260 A1 * | 8/2002 | Morris et al. ............ 606/41 |

\* cited by examiner

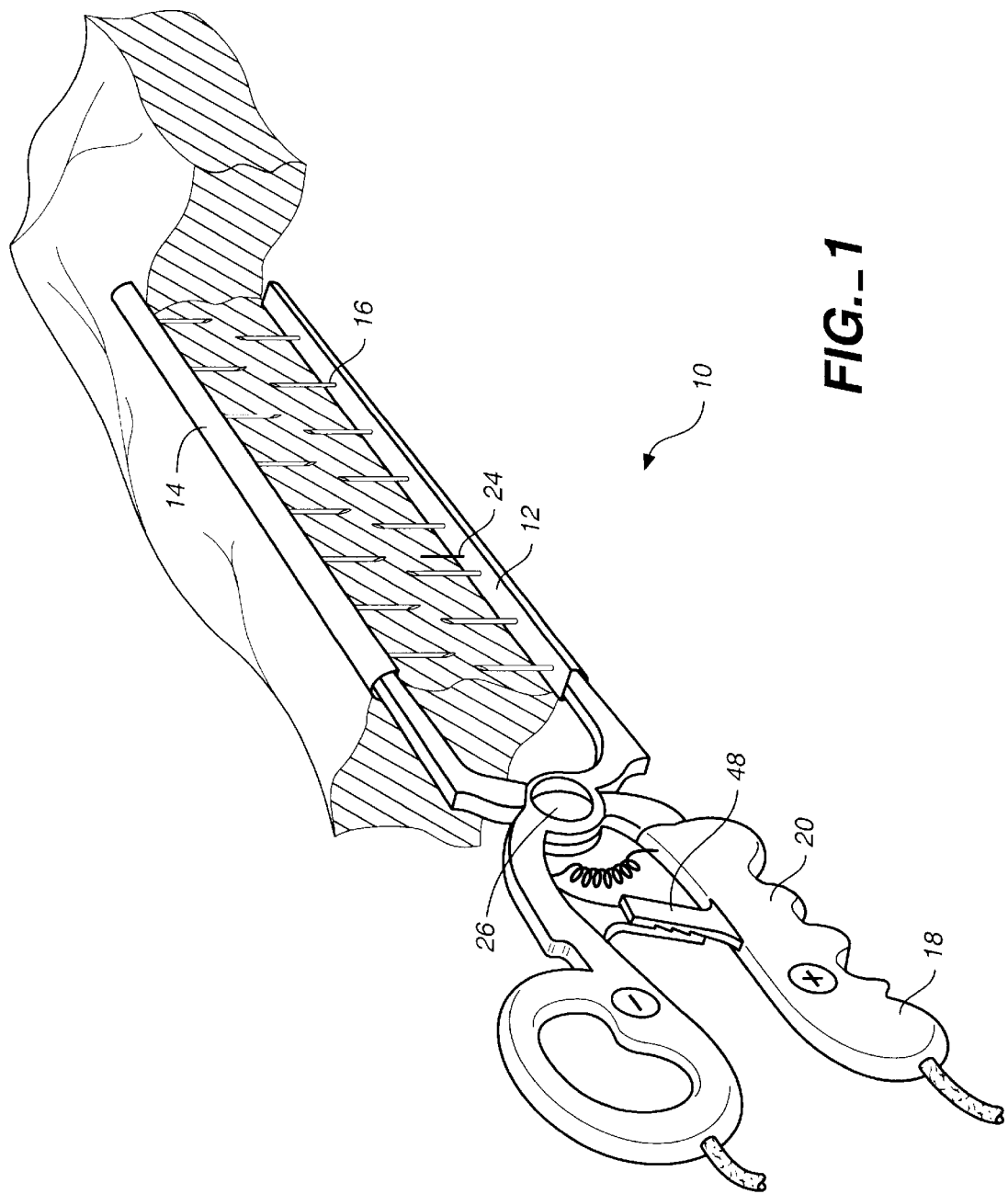

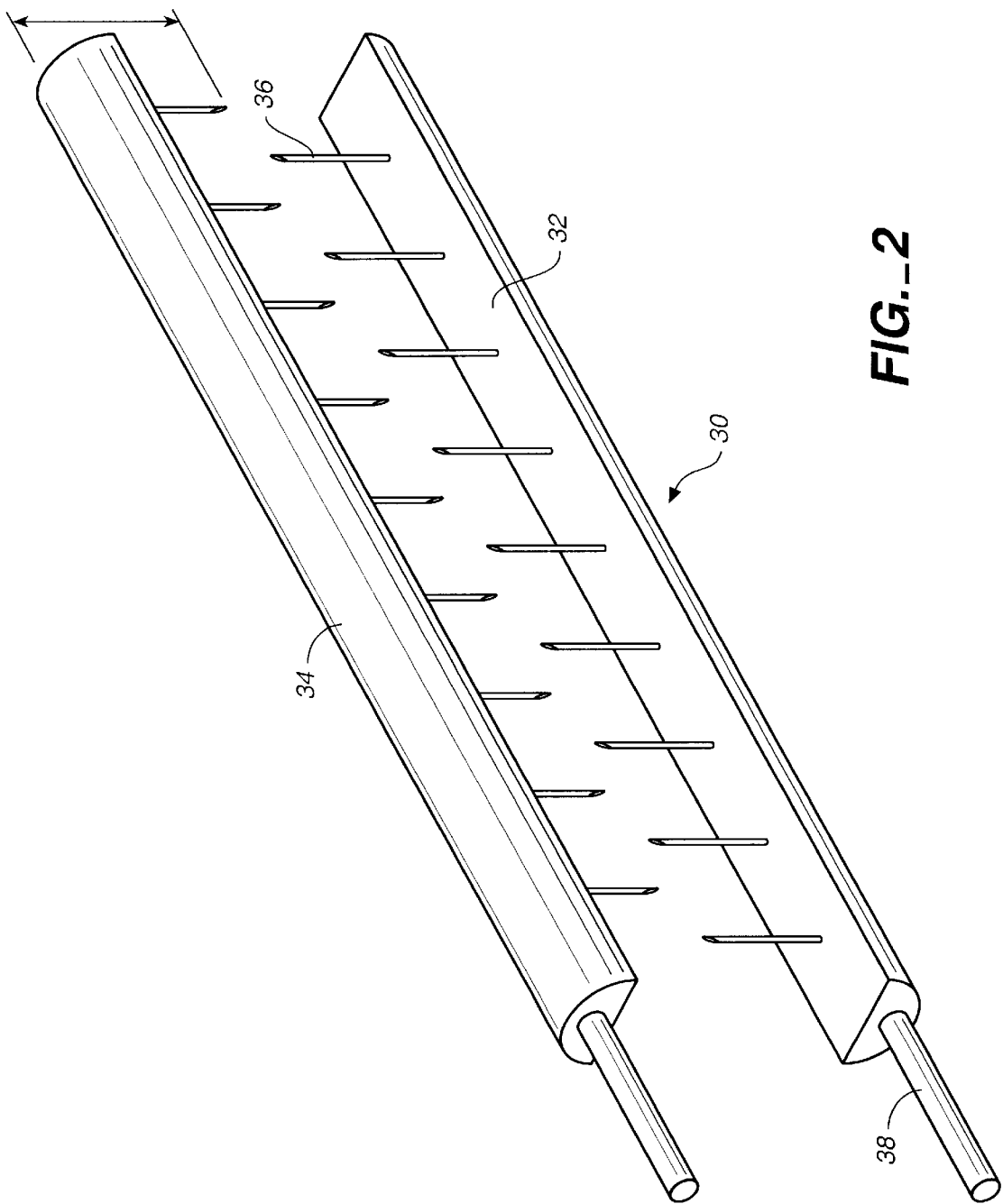
FIG._2

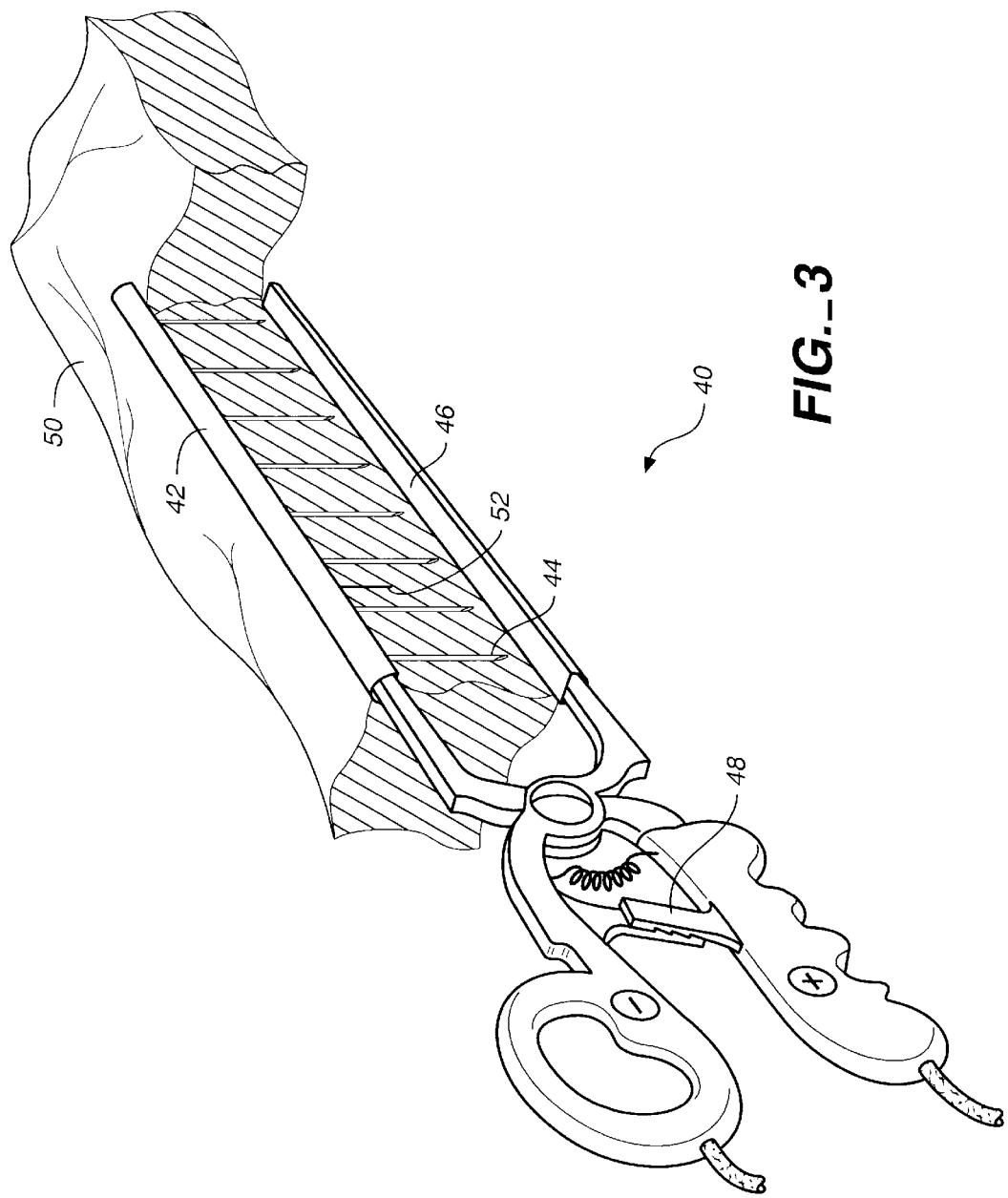

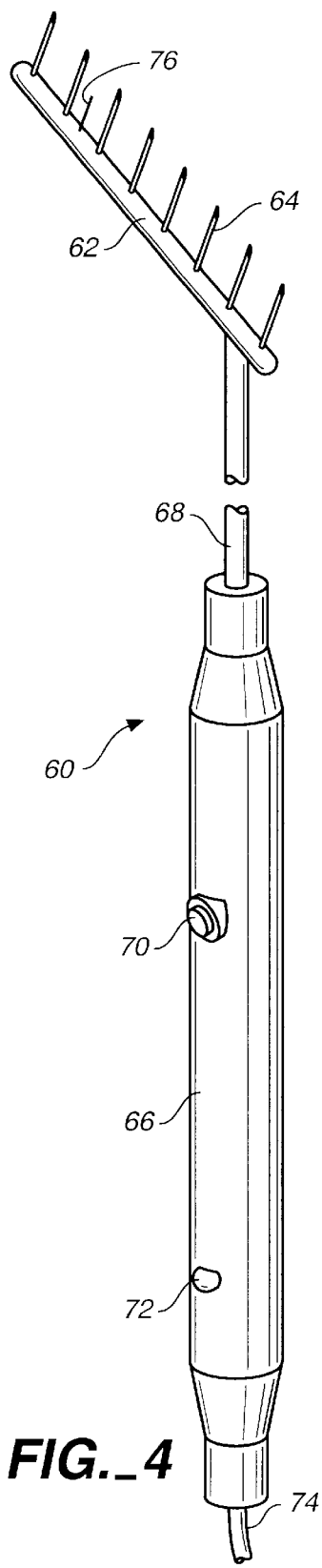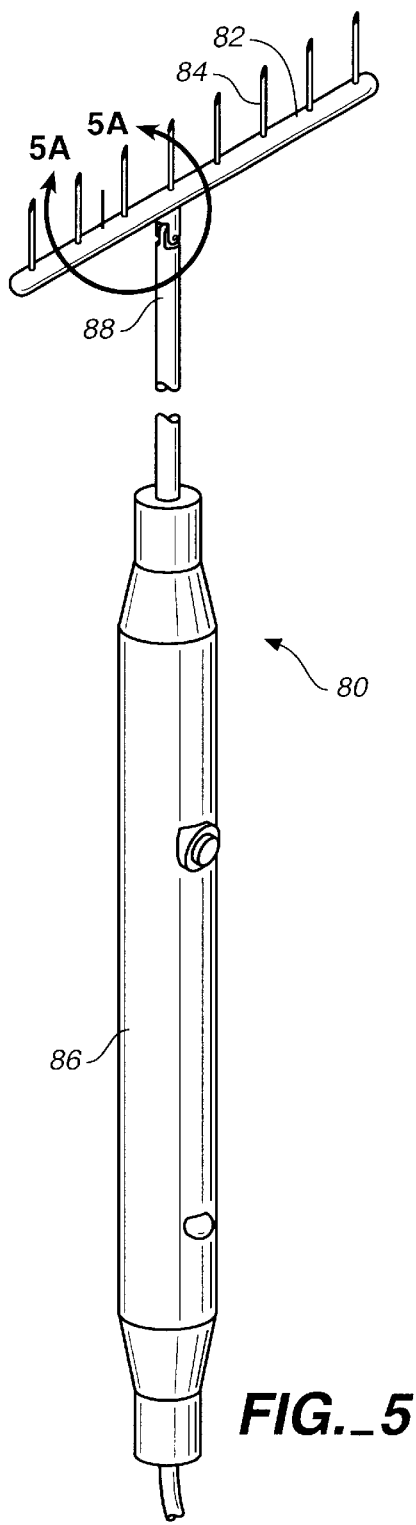

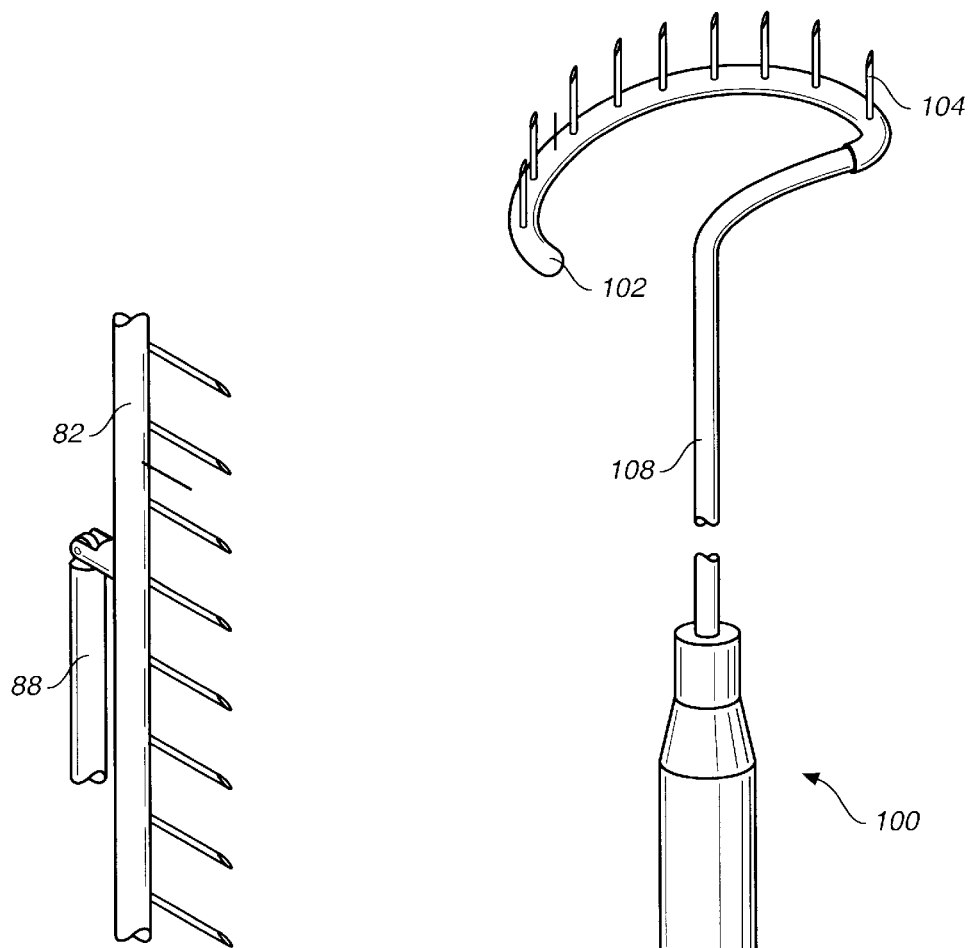
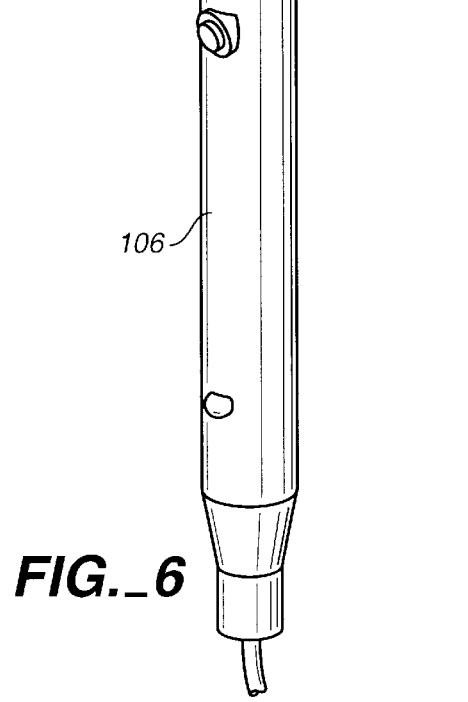
FIG._5A
FIG._6

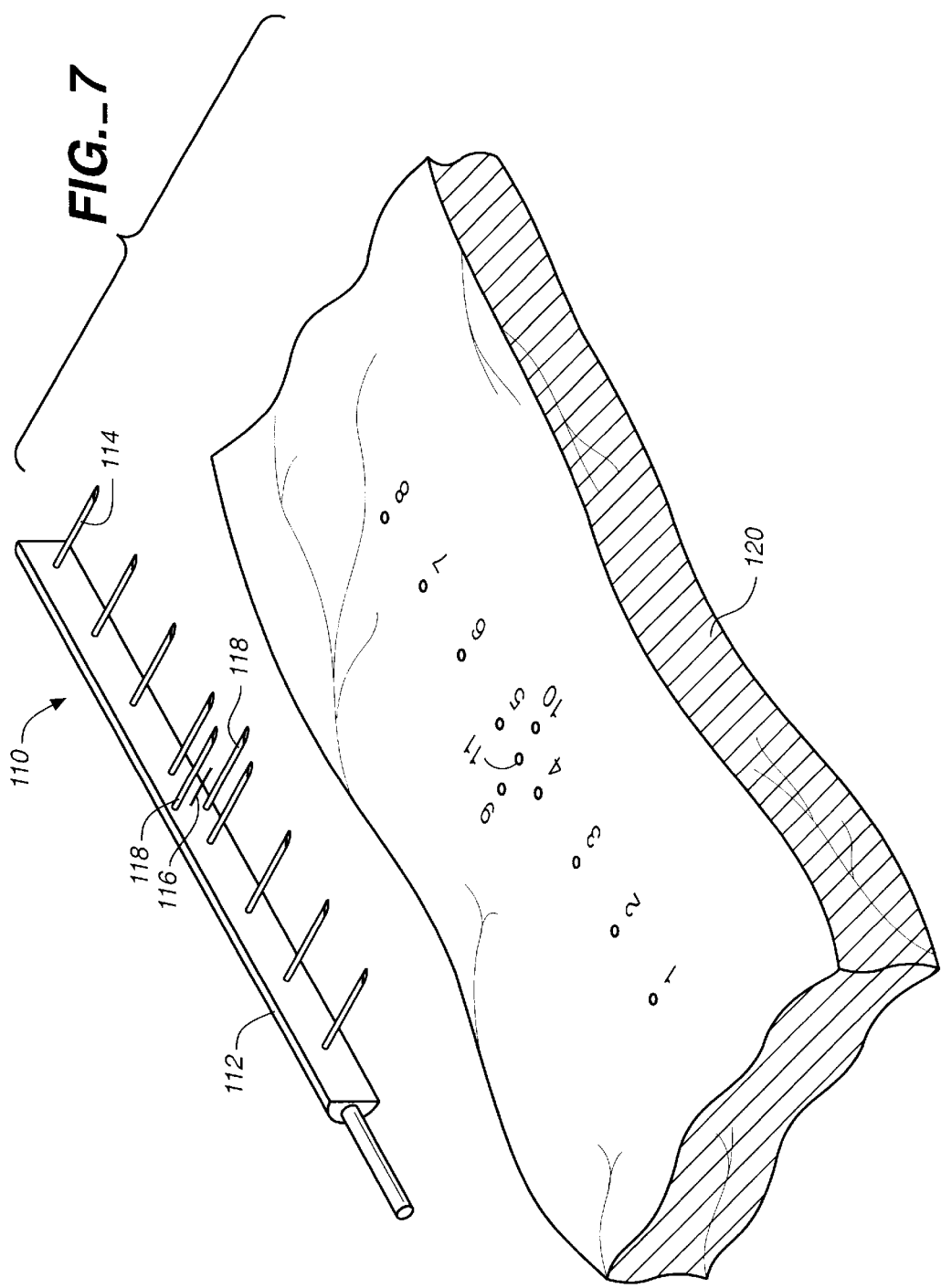
FIG._7

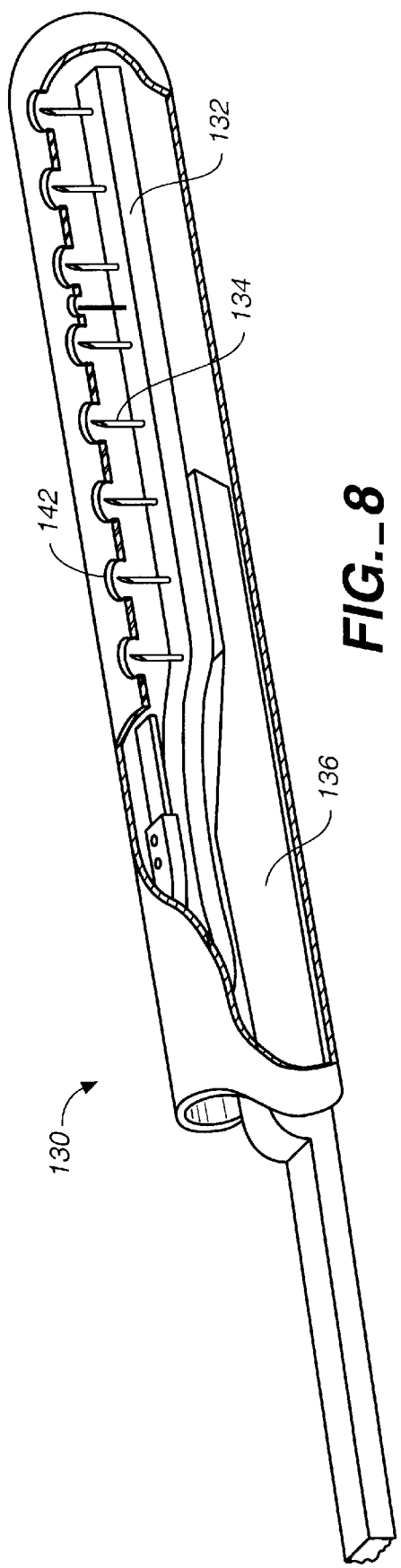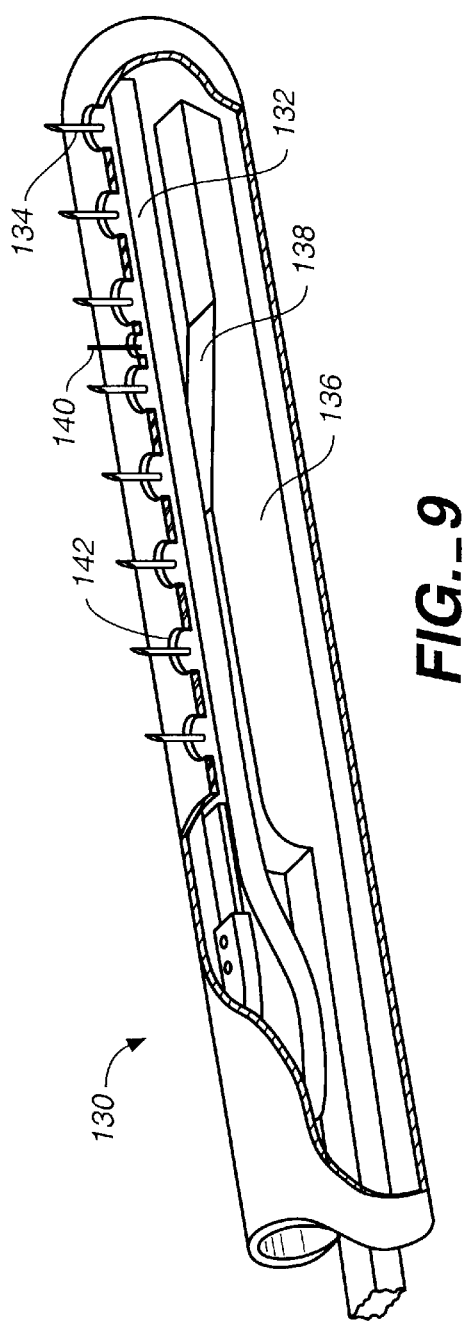

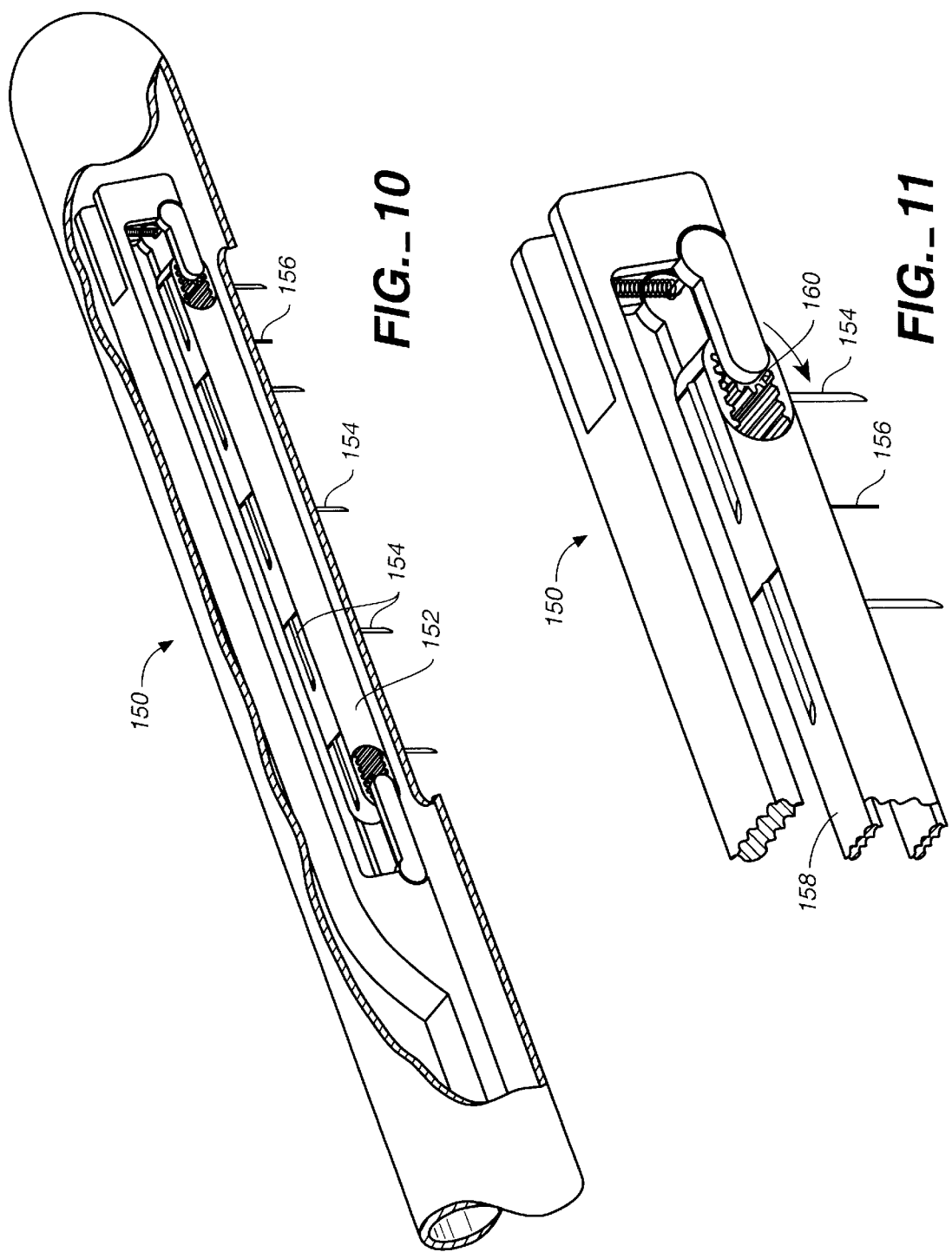

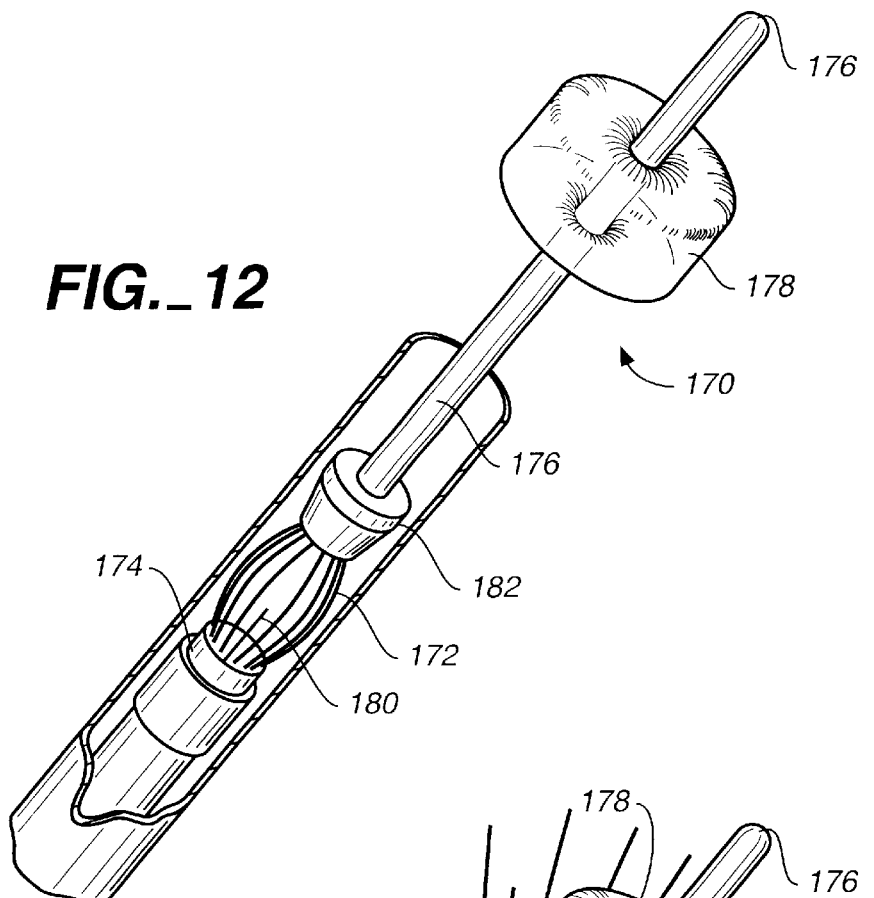
FIG._12
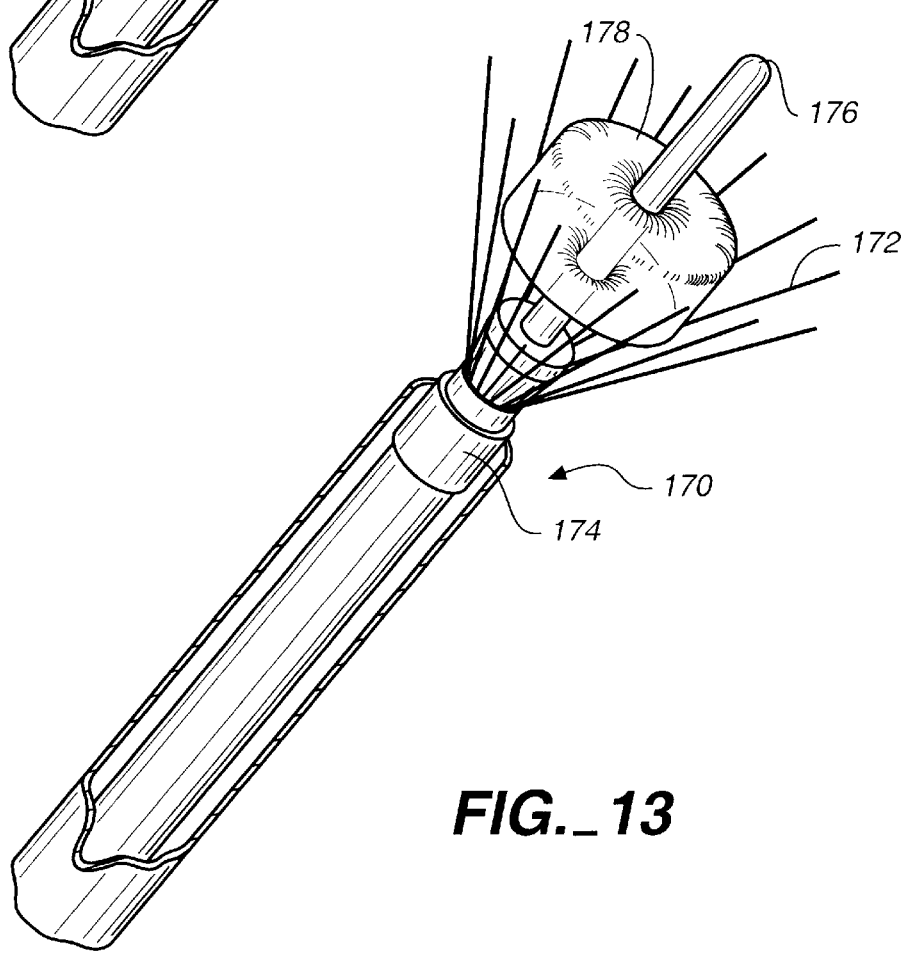
FIG._13

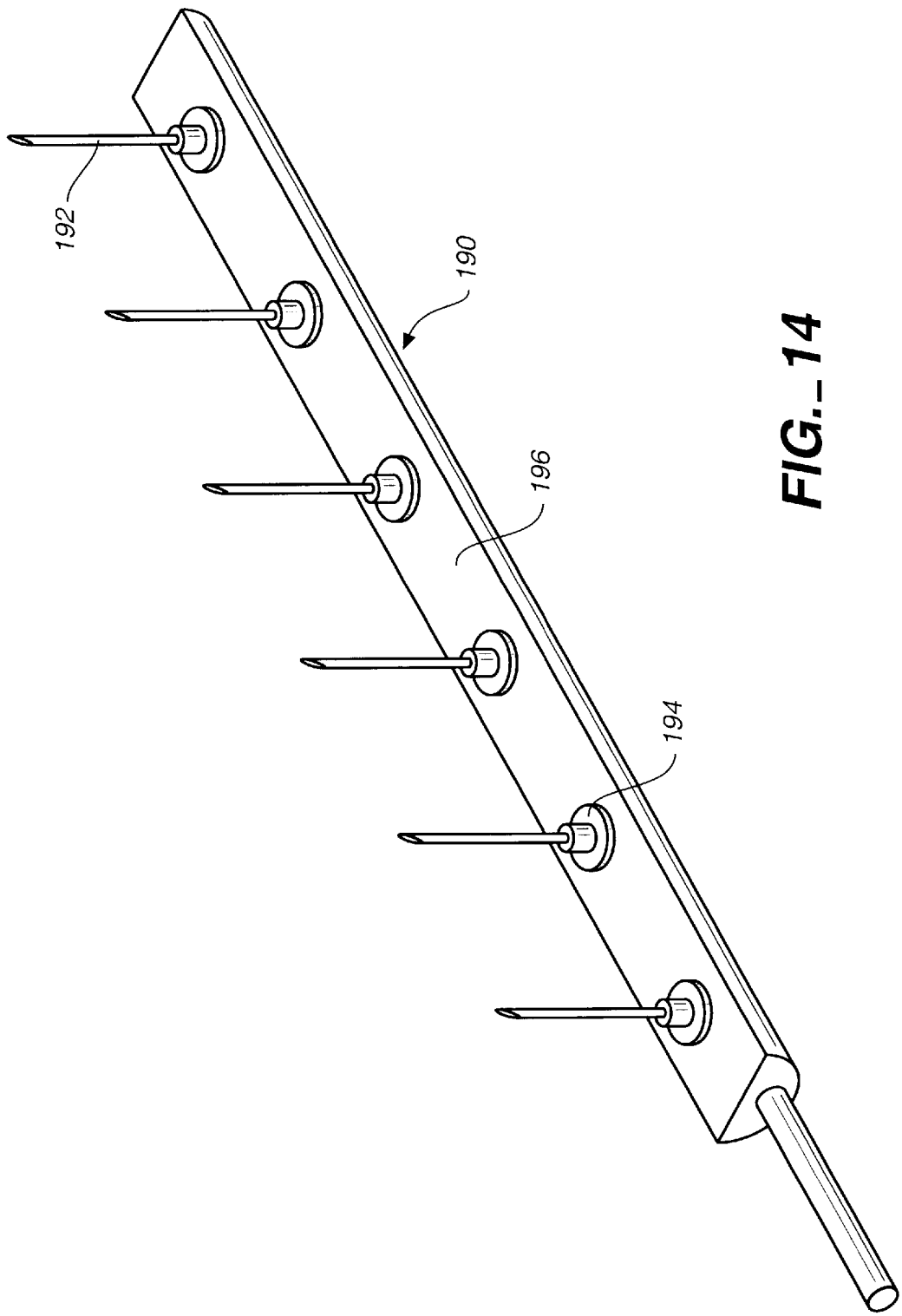
FIG._14

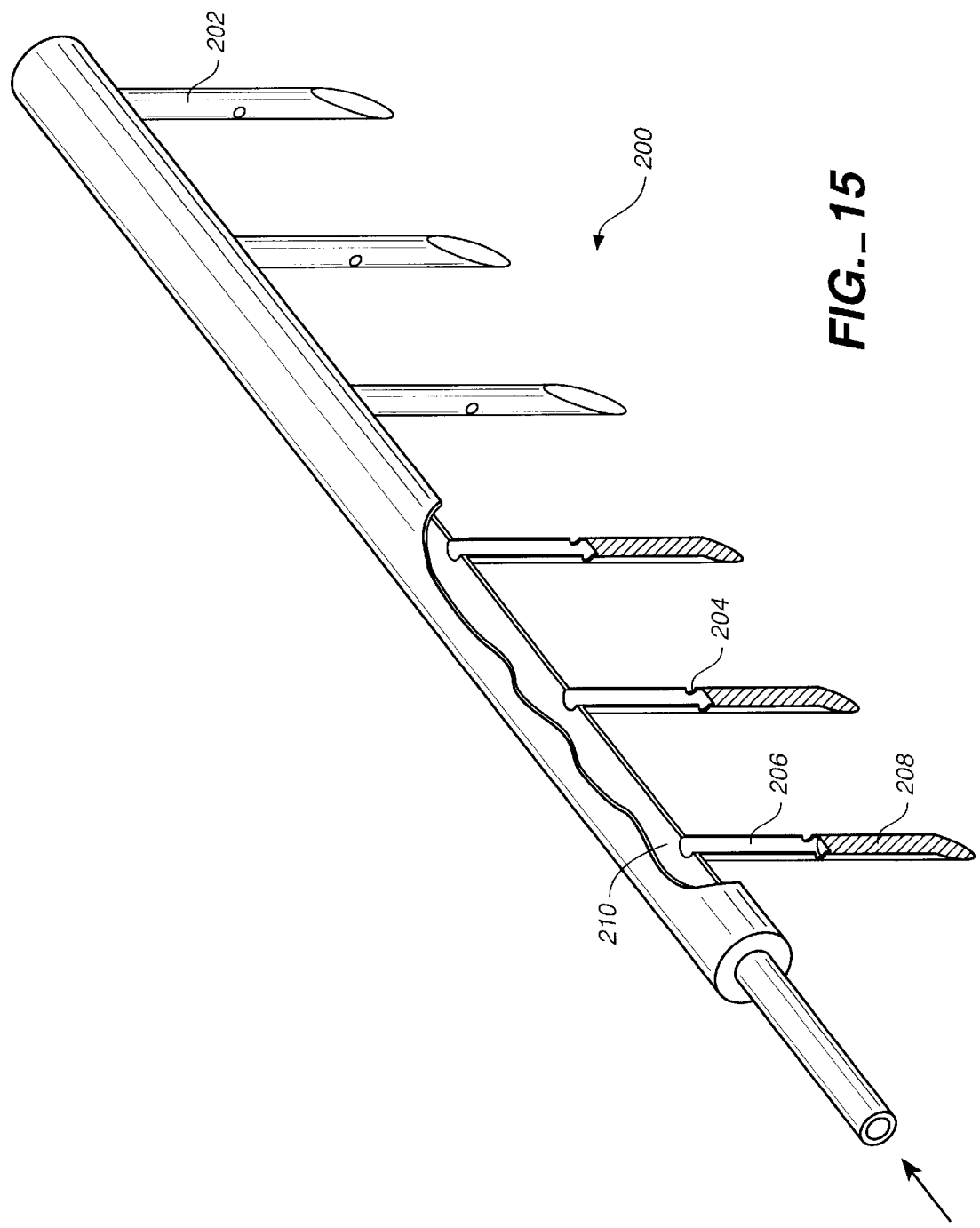
FIG._15

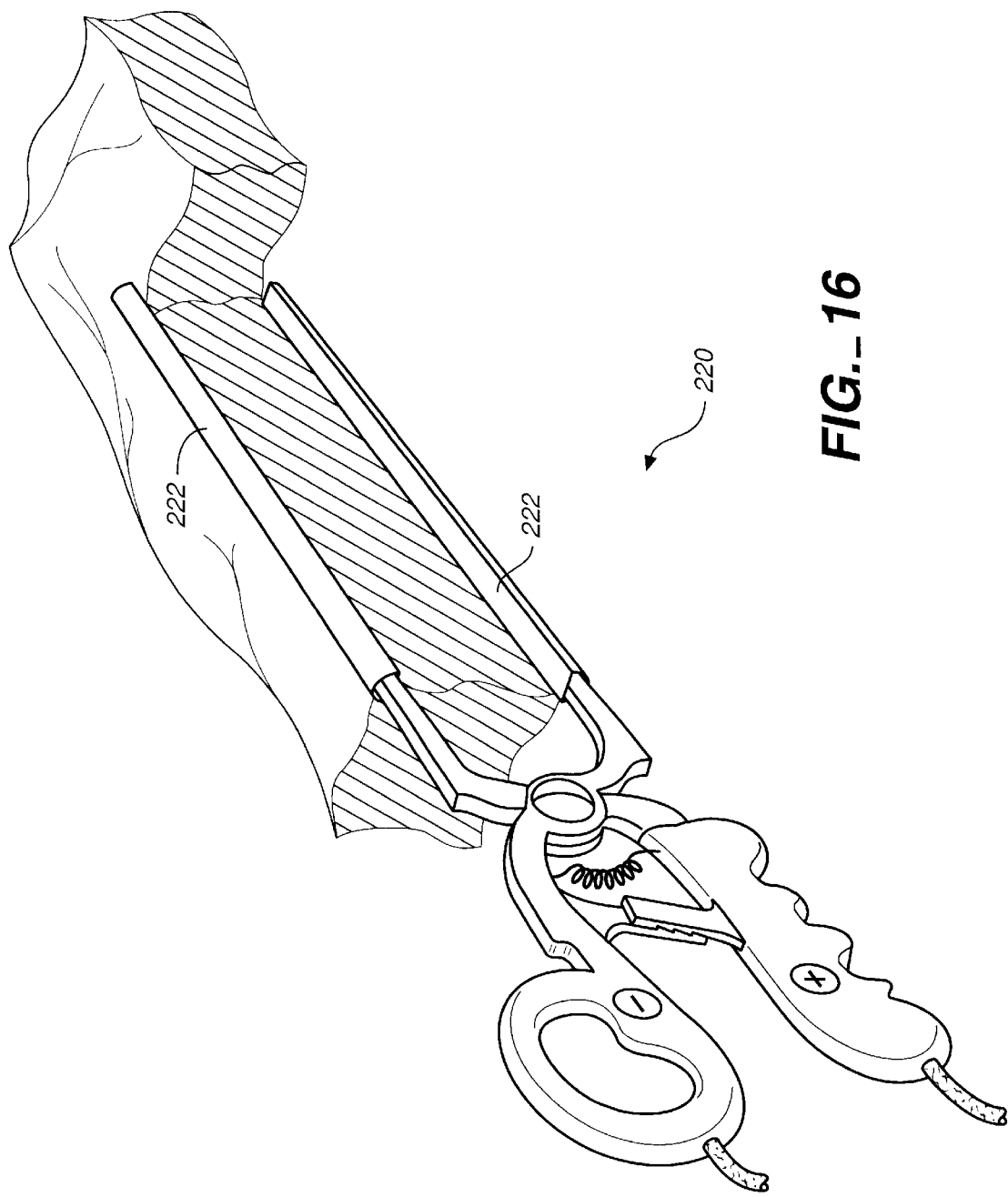

ATRIAL FIBRILLATION RF TREATMENT DEVICE AND METHOD

CROSS REFERENCE TO RELATED APPLICATIONS

This application claims priority under 35 U.S.C. §119(e) to U.S. Provisional Application Serial No. 60/256,245 filed on Dec. 15, 2000 and U.S. Provisional Application Serial No. 60/287,798 filed on Apr. 30, 2001, both of which are incorporated herein by reference in their entirety.

FIELD OF THE INVENTION

The invention relates to an atrial fibrillation RF treatment device and method, and more particularly, the invention relates to a device and method for creating a narrow transmural lesion or discontinuity in tissue, such as heart tissue or other body organs or tissues.

DESCRIPTION OF THE RELATED ART

Atrial fibrillation is a condition of the heart in which abnormal electrical signals are generated in the myocardial tissue causing irregular beating of the heart. One method used to treat atrial fibrillation is called the Maze procedure. The Maze procedure involves forming barriers in the heart tissue to prevent the abnormal electrical signals from passing through the heart. The barriers are created by forming several long (i.e., approximately 2–10 cm) scars. The scars are formed by cutting through the heart wall and sewing the wall back together to create the scars which are intended to stop the irregular beating of the heart by preventing the passage of abnormal currents. This procedure is referred to as the Maze procedure because it creates a maze of scars blocking the passage of abnormal electrical currents through the heart. These scars may be formed by cutting or by application of energy.

Procedures for forming the linear scars involve opening the patients chest cavity and forming linear incisions or cuts through the heart wall in specific locations described as the Maze III and other similar atrial fibrillation treatments.

The Maze III procedure using conventional surgical incisions has a success rate of up to 90%. A new technique of cryo-ablation has also been used to create the lesions in the heart wall. This approach has the benefit of reducing the cardiopulmonary bypass pump time and allowing more time for correcting the valvular disease and CABG if needed.

Although catheter techniques have been attempted for minimally invasive treatment of atrial fibrillation, these techniques have not been successful to date. Known catheter devices for forming these lesions include flexible catheters which form lesions from an interior surface of the heart. Examples of these ablation catheters are described in U.S. Pat. Nos. 5,895,417; 5,941,845; and 6,129,724 which are incorporated herein by reference in their entirety.

One drawback with the catheter techniques and devices used on the epicardial surface of the heart is that it is difficult to impossible to assure a transmural lesion or the complete blockage of unwanted electrical signals. In addition, RF energy will not go through fat with currently available devices because of the high impedance of the fat compared to the low impedance of tissue. In addition, current devices have difficulty dealing with varying thickness of tissue through which a transmural lesion is desired. Accordingly, it would be desirable to provide a system for precisely creating transmural lesions on a beating heart or non-beating heart with a minimum of trauma to the patient.

SUMMARY OF THE INVENTION

The present invention relates to a device and method for creating a transmural lesion.

In accordance with one aspect of the present invention, an RF treatment device for creating transmural lesions in tissue includes an electrode holder; a plurality of tissue penetrating RF needle electrodes arranged in a single linear array to create a continuous transmural lesion, each of the RF needle electrodes having a length of at least 4 mm; and an RF energy source connected to each of the RF needle electrodes with alternating electrodes connected to opposite polarities of the RF energy source.

In accordance with an additional aspect of the present invention, an RF treatment device for creating transmural lesions in heart tissue includes an electrode holder; a plurality of tissue penetrating RF needle electrodes arranged in a single linear array to create a continuous transmural lesion, each of the RF needle electrodes having a length sufficient to create a transmural lesion through the entire thickness of the tissue of the heart wall; and an RF energy source connected to each of the RF needle electrodes.

In accordance with a further aspect of the invention, a method of treating atrial fibrillations includes the steps of: penetrating heart tissue to be treated with an RF treatment device comprising a plurality of tissue penetrating RF needle electrodes arranged in a single linear array; and applying radio frequency energy to form a transmural lesion which provides a barrier across an entire thickness of the heart tissue to prevent the passage of abnormal electrical currents through the heart tissue.

In accordance with another aspect of the invention, a method of treating atrial fibrillations includes the steps of: positioning a first electrode of a radio frequency forceps on an endocardial surface of a heart at a location to be treated; positioning a second electrode of the radio frequency forceps on an epicardial surface of the heart opposite the first electrode; and applying radio frequency with the first and second electrodes to form a transmural lesion which provides a barrier to the passage of abnormal electrical currents through the heart tissue.

In accordance with another additional aspect of the present invention, a medical device for creating transmural lesions in tissue includes an electrode holder; a plurality of tissue penetrating needle electrodes arranged in a single linear array to create a continuous narrow lesion, each of the needle electrodes having a length sufficient to create a transmural lesion through the tissue of the heart wall; and an energy source connected to each of the needle electrodes.

BRIEF DESCRIPTION OF THE DRAWING FIGURES

The invention will now be described in greater detail with reference to the preferred embodiments illustrated in the accompanying drawings, in which like elements bear like reference numerals, and wherein:

FIG. 1 is a perspective view of a RF treatment device with two RF electrode holders and multiple electrodes.

FIG. 2 is a perspective view of an alternative embodiment of a treatment device with two electrode holders and multiple electrodes.

FIG. 3 is a perspective view of a treatment device with a single electrode holder having multiple electrodes and an anvil opposite the electrode holder.

FIG. 4 is a perspective view of a treatment device with a single electrode holder having multiple electrodes for application from an epicardial side of the heart.

FIG. 5 is a perspective view of a treatment device with a single hinged electrode holder having multiple electrodes.

FIG. 5A is an enlarged view of the device of FIG. 5 with the electrode is a rotated position.

FIG. 6 is a perspective view of a treatment device with a single curved electrode holder having multiple electrodes.

FIG. 7 is a perspective view of a treatment device with a thermocouple and electrodes for measuring temperature and electrical potential.

FIG. 8 is a partial cross sectional perspective view of a treatment device with retractable electrodes in a retracted position.

FIG. 9 is a partial cross sectional perspective view of the device of FIG. 8 with the electrodes in an extended position.

FIG. 10 is a partial cross sectional perspective view of a treatment device with retractable electrodes in an extended position.

FIG. 11 is an enlarged perspective view of a portion of the device of FIG. 10.

FIG. 12 is a partial cross sectional perspective view of a treatment catheter device with electrodes in a retracted position.

FIG. 13 is a partial cross sectional perspective view of the device of FIG. 12 with the electrodes in an extended position.

FIG. 14 is a perspective view of a treatment device with hollow needle electrodes for sealing holes created in the tissue.

FIG. 15 is a partial cross sectional perspective view of a treatment device with electrodes having holes for sealing holes created in the tissue.

FIG. 16 is a perspective view of a forceps type RF treatment device without tissue penetrating electrodes.

DETAILED DESCRIPTION OF THE INVENTION

FIG. 1 shows a first embodiment of an RF treatment device 10 with two radio frequency electrode holders 12, 14 each having multiple electrodes 16 arranged to create a transmural lesion through tissue. The treatment device 10 is placed with one electrode holder 12 placed on the endocardial surface of the heart wall with the electrodes 16 protruding towards the epicardial surface of the heart and the other electrode holder 14 placed on the epicardial surface of the heart with the electrodes protruding towards the endocardial surface of the heart forming a bipolar arrangement of equally spaced electrodes. The electrodes 16 are of an RF conducting material, such as, stainless steel.

A handle 18 of the device 10 is provided to position the electrodes 16 with a minimal force through any fat on the surfaces of the tissue and into the heart tissue. Preferably, the handle 18 provides a mechanism to hold the positive electrode holder 14 parallel to the negative electrode holder 12 and assure the electrodes 16 are parallel and equally spaced apart in a linear array. As will be discussed below, the linear array of electrodes may form a straight line, a curved line, a zig zag shape or other desired shape to form a continuous narrow lesion. Radio frequency energy is applied between the positive electrodes 16 on a positive electrode holder 14 and the negative electrodes 16 on the negative electrode holder 12 so that a transmural lesion is formed between each positive and negative electrode.

The embodiments of the present invention will be described below for use in creating a transmural lesion in heart tissue to treat atrial fibrillation by blocking the passage of abnormal electrical currents through the heart. However, it should be understood that the devices and methods described herein may also be used to create continuous transmural lesions in heart tissue and other body organs and tissues to treat other conditions. The basic principles discussed herein apply to the creation of a narrow transmural lesion through any conductive layer of material or tissue of varying thicknesses.

As used herein the term "transmural lesion" means a tissue lesion which completely transverses the tissue of a heart wall, an organ, or other tissue and causes a complete blockage of unwanted electrical signals through the tissue.

The RF treatment device 10 of FIG. 1 includes a controller 20 which may be positioned within the handle 18 or otherwise attached to the treatment device 10. Preferably, a thermocouple or temperature sensing member 24 is arranged on one of the electrode holders 12, 14 and is connected to the controller 20 to provide feedback to the controller of the temperature of the tissue. The temperature sensing member 24 is preferably arranged equal distance between the two center most electrodes (one positive and one negative), but can be between any two electrodes to measure the temperature of the tissue. The controller 20 controls the power delivered to the tissue to attain and maintain a preferred temperature of about 65 degrees Centigrade with a range of about 60–95 degrees Centigrade.

Since fat has significantly higher impedance than tissue, RF energy goes uniformly though tissue and not fat. The RF treatment devices of the present invention provide an advantage over known devices which deliver RF energy to the surface of the heart or penetrate a small distance into the heart tissue but not through the fat. By penetrating through the fat and delivering the RF energy directly to the tissue, the present invention is able to create a continuous transmural where other devices create a discontinuous lesion or a lesion which does not extend all the way through the tissue.

In addition, blood has about the same impedance as the tissue and blood is a tremendous dissipater of heat energy. Thus, the flow of blood within the heart does not coagulate during formation of the lesion even if exposed to RF energy.

The RF treatment device of FIG. 1 includes electrodes 16 having a preferred diameter of about 0.022 inches (0.56 mm), but can have a range of diameters 50% greater or smaller. The preferred length of the electrodes is at least 4 mm to ensure that the electrodes 16 pass through any fat lying on a surface of the heart tissue and into the heart tissue itself. Preferably, the electrodes have a length of about 5 mm to about 15 mm, and more preferably about 8 mm. The electrodes in both electrode holders 12, 14 are spaced at a preferred distance of about 8 mm, but can range from about 6 mm to about 10 mm such that when both electrode holders are in position the distance between the adjacent positive and negative electrodes is preferably about 4 mm, with a range of about 3 mm to about 5 mm. The electrodes 16 are preferably sharpened like a hypodermic needle for easy penetration through the heart wall.

FIG. 2 shows a heat treatment device 30 which operates in a manner similar to the RF treatment device of FIG. 1. The heat treatment device 30 includes two electrode holders 32, 34 with multiple electrodes 36 arranged in an alternating linear fashion as in the embodiment of FIG. 1. The lesions are formed by applying heat energy including either cryoablation, thermoelectric cooling, heating with heat pipes, or other known heating or cooling techniques or RF energy. The electrode holders 32, 34 may be arranged on the legs of a forceps device as described above with respect to FIG. 1. Alternatively, the electrode holders 32, 34 may be positioned on the ends of catheters or other medical devices in which case a controller will be used to accurately locate the electrodes on opposite sides of the heart tissue.

FIG. 3 shows an alternative embodiment of a treatment device 40 with all of the electrodes 44 (positive and negative) mounted in a single electrode holder 42 placed on the epicardial surface of the heart 50 with the electrodes protruding towards the endocardial surface. The electrodes 44 are arranged in a bipolar arrangement of equally spaced electrodes with alternating polarities. The treatment device 40 includes an anvil 46 that is placed inside the heart. The anvil 46 supports the tissue for penetration of the radio frequency, cryo-ablation, thermoelectric, or other electrodes 44 and assures that the electrodes easily penetrate all the way through the heart wall. The electrodes 44 may touch the anvil 46, protrude into the anvil, or be spaced slightly from the anvil. Preferably, the electrodes completely transverse the tissue. A handle 48 is provided to hold the electrode holder 42 parallel to the anvil 44. In addition, a temperature sensing member 52 is provided to provide feedback to a controller to control the application of energy.

FIG. 4 illustrates a treatment device 60 with a single electrode holder 62 and a single array of electrodes 64 similar to the device of FIG. 3, except there is no anvil. The electrodes 64 are sharpen adequately to allow penetration through the heart wall without the use of an anvil and there is no need for the anvil mechanism shown in FIG. 3. As in the embodiments above, a temperature sensing member 76 is provided between electrodes. At the proximal end of the electrode holder 62 the electrode holder is connected to a handle 66 by a stem 68 of sufficient length and formability to allow transthoracic procedures. The handle 66 contains a power control switch 70, a power indicator light 72, and a cable 74 for connection to an energy source.

The electrodes 44 in the embodiment of FIG. 4 and in other embodiments with a single electrode holder are preferably of sufficient length to completely transverse the tissue and even protrude out an opposite side. The electrodes are preferably at least 4 mm long.

FIGS. 5 and 5A show a treatment device 80 including an electrode holder 82 and a plurality of electrodes 84 arranged in an array on the electrode holder. The electrode holder 82 is connected to a handle 86 by a stem 88. The stem 68 is pivotally connected to the electrode holder 82 to improve maneuverability for transthoracic procedures. As shown in FIG. 5A, the electrode holder 82 can be pivoted 90 degrees in two directions to achieve a desired orientation of the parallel electrode array.

FIG. 6 illustrates a treatment device 100 having an electrode holder 102 with a curved shape. The electrode holder 102 supports an array of electrodes 104 in a curved linear array. As in previous embodiments, the electrode holder 102 is supported on a handle 106 by a stem 108 which is preferably a flexible shaft. The electrode holder 102 is configured to fit the anatomical need to stop atrial fibrillation in specific locations of the heart, such as around the pulmonary veins. The electrodes 102, their length, diameter, and spacing are the same as in previous embodiments. The different shapes may also be provided with different curvatures and in different sizes.

FIG. 7 is a probe or catheter type treatment device 110 with an electrode holder 112 at the distal end containing a plurality of positive and negative electrodes 114. The treatment device 110 of FIG. 7 also includes a temperature sensing member 116, such as a thermocouple, and two additional diagnostic electrodes 118. The diagnostic electrodes 118 are located about 1 mm to about 2 mm on each side of a line through a centerline of the electrodes 114. The diagnostic electrodes 118 may be used to measure the potential across the lesion to assure the electrodes 114 are properly placed across an atrial fibrillation pathway and/or to assure total blockage of the atrial fibrillation pathway before the electrodes are removed from the heart wall. FIG. 7 also shows the pattern of holes formed in the heart tissue 120 by the electrodes 114 (holes 1–8), the temperature sensing member 116 (hole 11), and the diagnostic electrodes 118 (holes 9 and 10). The electrical potential is preferably measured between the diagnostic electrodes. In addition, the electrical potential may be measured between electrodes 114, 118 and sensing member 116, for example, measured between holes 4–9, 4–11, 5–9, 5–10, 9–11, and 10–11 to gain electrical signal vector information.

FIGS. 8 and 9 illustrate a probe or catheter type treatment device 130 having electrode holder 132 at a distal end with a plurality of positive and negative electrodes 134. A mechanical pusher arm 136 within the catheter device 130 acts as a cam to cause the electrodes to extend from or retract into the catheter device. As shown in FIG. 8, when the mechanical pusher arm 136 is in a proximal position the electrodes 134 are retracted entirely within the distal end of the treatment device 130. When the mechanical pusher arm 136 is advanced to the distal position illustrated in FIG. 9, a ramp 138 on the pusher arm moves the electrodes 134 and the temperature sensor 140 to extended positions at which the electrodes and temperature sensor project through openings 142 in the device. The openings 142 may be one or more holes, as shown, or may be slots.

FIGS. 10 and 11 illustrate another probe or catheter type treatment device 150 having an electrode holder 152 at a distal end with a plurality of positive and negative electrodes 154 and a temperature sensor 156. The electrode holder 152 includes a circular track 158. As the catheter device 150 is advanced along the heart wall tissue, the electrodes 154 rotate out to 90 degrees with respect to the catheter and sequentially enter the heart wall tissue. At a proximal end of the track 158 the electrodes 154 are pulled out of the tissue, retracted into the catheter, and lay flat on the track. FIG. 11 is an enlarged view of a portion of the distal end of the device 150 showing more clearly the track 158 and a wheel 160 for supporting the track.

FIGS. 12 and 13 show an alternative catheter treatment device 170 in which a plurality of positive and negative electrodes 172 and a temperature sensor 180 are advanced out of a distal end of the catheter or through openings in the catheter. The electrodes 172 are advanced out the end of a catheter sheath from a retracted delivery position (FIG. 12) to an extended treatment position (FIG. 13) by a pusher mechanism 174. The electrodes 172 are advanced in a circular manner to create a circular lesion, such as around a pulmonary vein. A center lumen of the catheter device 170 is used to advance a guidewire 176 upon which is mounted a distal tip locator and/or balloon 178 to position the center of the catheter in the center of the pulmonary vein opening. Preferably, the electrodes 172 are flared to a desired diameter by a conical member 182 on the guidewire 176.

FIGS. 14 and 15 illustrate alternative embodiments of treatment devices including ways to add an FDA approved glue, sealant, hemostat, mechanical plug, or other material around the electrodes to seal or encourage sealing of the holes created by the electrodes. A treatment device 190 of FIG. 14 includes hollow electrodes 192 for delivery of a liquid or paste into the holes created by the electrodes. The electrodes may be partially or fully hollow. In addition, or in place of the hollow electrodes, a mechanical plug 194 or disk may be positioned on the electrode holder 196 around each of the electrodes to seal the holes after removal of the electrodes. Alternatively, a strip of plug material may be used in place of the disks 194.

FIG. 15 shows a treatment device 200 in which the electrodes 202 (and possibly temperature sensing member) include side holes 204, a partially hollow central portion 206, and a plugged distal end 208 for delivery of one of the sealants described above to the holes in the tissue. The sealant delivered through a hollow body 210 of the device 200 to stop the potential leakage of blood from the heart wall.

Another method of sealing the holes in the heart tissue is to continue delivery of RF energy or other energy at full or partial power during extraction of the electrodes from the tissue. Further, the RF energy or other energy may be used to aid in delivery of a sealant or glue by melting the material. The holes may also be sealed naturally by coagulation caused by residual warmth in the tissue after application of the energy.

One example of the parameters used to create a transmural lesion with the devices described above is about 10–25 watts of power applied for about 20–40 seconds to achieve a temperature of about 65–75 degrees Centigrade. This system achieves a very narrow and complete transmural scar in heart tissue. The lesion has a narrow width which is preferably about 1 to about 3 mm.

In use of the forceps type treatment devices described above, one of the electrode holders 12 or legs of the forceps is inserted into the heart through an incision and is positioned on the endocardial surface of the heart at the location identified for treatment. The other electrode holder 14 or leg of the forceps is positioned on the epicardial surface of the heart. The legs of the forceps are brought together on opposite sides of the heart wall and bi-polar RF energy is applied to create a burn or lesion that is transmural or extends completely through the heart tissue.

The forceps of FIG. 1 are designed to create a lesion in a straight line. Other forceps may be curved to form a transmural lesion with a curved or semicircular pattern. The semicircular lesion pattern may be used to create a lesion pattern that includes the four pulmonary veins. The straight forceps may be used to create an ablation at the vena cava intersection and for the right ventricle in the area of the tricuspid valve. In addition, the curved forceps of may be used for treatment at the base of the atrial appendix. The forceps shapes and uses illustrated and described are merely examples of some of the shapes which may be used to reach different parts of the heart. It should be understood that other shapes may also be used to reach other parts of the heart tissue to be treated.

The treatment according to the present invention can be done with or without extracorporeal circulation. The treatment may be performed on a beating or stopped heart. When beating heart surgery is performed the leg of the forceps which enters the heart is preferably provided with a seal, gasket, or suture to prevent blood leakage at the incision.

A hinge 26 of the forceps shown in FIG. 1 and in other embodiments of the invention is preferably an adjustable hinge to keep an even pressure along the entire length of the electrodes provided on the legs of the forceps. The hinge preferably provides a means of keeping the legs of the forceps parallel and to accommodate tissue thicknesses from about 1–15 mm.

A length of the electrode holders in the various embodiments of the invention may vary depending on the length of the lesion desired. For example the length of the electrode holders may be about 1 cm to about 10 cm.

The embodiment of FIG. 16 is a treatment device 220 with flat electrodes 222 positioned on opposite surfaces of the heart tissue without tissue penetrating electrodes. The tissue contacting faces of the electrodes 222 preferably have a flat tissue contacting surface with radius corners to best minimize the width of the treatment zone and prevent current concentration at the corners. The electrodes may be sandwiched between insulating layers and measuring electrodes. The measuring electrodes are provided upon opposite sides of the RF electrodes and are used for measuring the potential across the lesion. The measurement of the potential across the lesion is used to determine whether treatment is complete. It may be desirable to roughen the tissue contacting surface of the electrode to allow the electrode to break or cut through the thin film of insulating tissue which forms a barrier on the endocardial and epicardial surfaces of the heart.

Although the present invention has been described with respect to the application of RF bi-polar energy, it should be understood that the forceps device according to the present invention may also be used to apply other types of energies, such as cryo, ultrasound, microwave, heat, or other electrical means of providing an interruption to the abnormal electrical circuits at given regions. These types of energy would be able to create a transmural barrier having a minimal width to block electrical currents. The length and curvature of the electrode and the corresponding lesion created can be designed to meet requirements of a particular treatment site.

Although electrodes having circular cross sections have been described as the preferred embodiments, other electrode cross sections may be used. Methods for attaching the electrodes to the electrode holders include molding, welding, the use of adhesive to attach electrodes to existing instruments, or the use of sleeves containing the electrodes which slide over the legs of the exiting forceps instruments.

The electrodes positioned on the electrode holders of the forceps type devices have been illustrated as brought together by manual force applied by the operator. However, the electrodes may be brought together by other means such as by magnets, springs, or the like.

One or more methods may be employed in any of the foregoing embodiments of the invention to facilitate electrode insertion. These methods include vibration, such as ultrasonic vibration, oscillation in any plane, rotation of the electrodes, sequential electrode insertion, coatings or lubricants on the electrodes, and tip geometries which aid in penetration. In addition, a holding device, such as a vacuum device, may be used to hold the treatment device to the tissue before and during penetration with the electrodes.

While the invention has been described in detail with reference to the preferred embodiments thereof, it will be apparent to one skilled in the art that various changes and modifications can be made and equivalents employed, without departing from the present invention.

What is claimed is:

1. An RF treatment device for creating transmural lesions in tissue, die device comprising:
   an electrode holder;
   a plurality of tissue penetrating RF needle electrodes arranged in a single linear array, without additional RF electrodes, to create a continuous trausmural lesion, each of the RF needle electrodes having a length of at least 4 mm; and an RF energy source connected to each of the RF needle electrodes with alternating electrodes connected to opposite polarities of the RF energy source.

2. The device of claim 1, wherein the linear array of RF needle electrodes forms a straight line.

3. The device of claim 1, wherein the linear array of RF needle electrodes forms a curved line.

4. The device of claim 1, wherein each of die RF needle electrodes has a length of about 5 mm to about 15 mm to completely transverse the tissue.

5. The device of claim 1, wherein each of the RF needle electrodes has a sharp tissue penetrating tip.

6. The device of claim 1, wherein the electrode holder is mounted on a catheter.

7. The device of claim 1, wherein the electrode holder is mounted on a non-catheter medical device.

8. The device of claim 1, further comprising an anvil movable with respect to the electrode holder to trap tissue between the electrode holder and the anvil.

9. The device of claim 8, further comprising a plurality of RF needle electrodes positioned on the anvil.

10. The device of claim 1, wherein the RF needle electrodes are retractable.

11. The device of claim 10, further comprising a cam element within the electrode bolder for moving the RF needle electrodes from a retracted position to an extended position.

12. The device of claim 10, wherein the RF needle electrodes are rotatable within the electrode holder from a retracted position to an extended position.

13. The device of claim 10, wherein the needle holder is a tubular member and the RF needle electrodes are contained within the tubular member in a retracted position and are pushed out of a distal end of the tubular member to an extended position.

14. The device of claim 1, wherein the RF needle electrodes include boles for delivery of a sealant.

15. An RF treatment device for creating transmural lesions in tissue, the device comprising;
an electrode holder:
a plurality of tissue penetrating RF needle electrodes arranged in a single linear array to create a continuous transmural lesion, each of the RF needle electrodes having a length or at least 4 mm; and
an RF energy source connected to each of the RF needle electrodes with alternating electrodes connected to opposite polarities of the RF energy source; and
a temperature sensing member positioned between two of the RF needle electrodes.

16. The device of claim 15, wherein the temperature sensing member is mounted on a tissue penetrating needle.

17. The device of claim 1, further comprising diagnostic electrodes positioned on tissue penetrating needles arranged on opposite sides of the linear array of RF needle electrodes.

18. The device of claim 1, wherein the RF needle electrodes are parallel.

19. The device of claim 1, further comprising means for aiding penetration of the tissue with the RF needle electrodes.

20. The device of claim 19, wherein the means for aiding penetration is vibration, oscillation, or impact.

21. An RF treatment device for creating transmural lesions in tissue, the device comprising:
an electrode holder;
plurality of tissue penetrating RF needle electrodes arranged in a single linear array to create a continuous transmural lesion, each of the RF needle electrodes having a length of at least 4 mm: and
an RF energy source connected to each of the RF needle electrodes with alternating electrodes connected to opposite polarities of the RF energy source; and
means for aiding penetration including coating or lubricants.

22. An RF treatment device for creating transmural lesions in heart tissue, the device comprising:
an electrode holder;
a plurality of tissue penetrating RF needle electrodes arranged in a single linear array, without additional RF electrodes, to create a continuous transmural lesion, each of the RF needle electrodes having a length sufficient to create a transmural lesion through the entire thickness of the tissue of the heart wall; and
an RF energy source connected to each of the RF needle electrodes with alternating electrodes connected to opposite polarities of the RF energy source.

23. The device of claim 22, wherein the RF needle electrodes having a length of at least 4 mm.

24. The device of claim 22, wherein the linear array of RF needle electrodes forms a straight line.

25. The device of claim 22, wherein the linear array of RF needle electrodes forms a curved line.

26. The device of claim 22, wherein the RF needle electrodes are parallel.

27. A method of treating atrial fibrillations comprising:
penetrating heart tissue to the treated with an RF treatment device comprising a plurality of tissue penetrating RF needle electrodes arranged in a single linear array, with alternating electrodes having opposite polarities; and
applying radio frequency energy to form a transmural lesion which provides a barrier across an entire thickness of the heart tissue to prevent the passage of abnormal electrical currents through the heart tissue.

28. The method of claim 27, wherein the heart tissue is penetrated from an endocardial surface of the heart.

29. The method of claim 27, wherein the heart tissue is penetrated from an epicardial surface of the heart.

30. The method of claim 27, wherein the heart tissue is penetrated with RF needle electrodes having a length sufficient to create a transmural lesion through the tissue of the heart wall.

31. The method of claim 27, wherein the heart tissue is penetrated with RF needle electrodes having a length sufficient to penetrate at least $2/3$ or the way through the heart wall.

32. The method of claim 27, further comprising a step of controlling the power delivered to the RF treatment device based on a temperature sensed within the heart tissue.

33. The method of claim 27, wherein the step of applying radio frequency energy forms a narrow transmural lesion with a width of about 1 mm to about 3 mm.

34. The method of claim 27, further comprising a step of applying a glue, sealant, hemostat or mechanical plug to prevent bleeding from the holes created by the RF needle electrodes.

35. The method of claim 27, further comprising retracting the RF needle electrodes front the heart tissue while applying radio frequency energy to assist in sealing the holes created by the RF needle electrodes.

36. The method of claim 27, further comprising controlling the application of radio frequency energy based on feedback from a temperature sensor and diagnostic electrodes.

37. A medical device for creating transmural lesions in tissue, the device comprising:

an electrode holder;

a plurality of tissue penetrating needle electrodes arranged in a single linear array, without additional RF electrodes, the single linear array with alternating electrodes having opposite polarities to create a continuous transmural lesion, each of the needle electrodes having a length sufficient to create a transmural lesion through the tissue of the heart wall; and an energy source connected to each of the needle electrodes.

38. The device of claim 37, wherein the electrodes are one of bipolar RF electrrodes, cryo-ablation electrodes, thermoelectic electrodes, heat pipe electrodes, and ultrasonic electrodes.

39. The device of claim 37, wherein the electrodes have a length of at least 4 mm to create the transmural lesion.

* * * * *